United States Patent [19]

Howie et al.

[11] Patent Number: 5,129,723
[45] Date of Patent: Jul. 14, 1992

[54] HIGH PERFORMANCE ZIMM CHROMATOGRAPHY—HPZC

[75] Inventors: Janet Howie, Goleta, Calif.; Christian Jackson, Wilmington, Del.; Philip J. Wyatt, Santa Barbara, Calif.

[73] Assignee: Wyatt Technology Corporation, Santa Barbara, Calif.

[21] Appl. No.: 684,714

[22] Filed: Apr. 11, 1991

[51] Int. Cl.$^5$ ............................................. G01N 21/51
[52] U.S. Cl. ..................................... 356/336; 356/343
[58] Field of Search ................. 356/336, 338, 343, 340

[56] References Cited

U.S. PATENT DOCUMENTS

| | | | |
|---|---|---|---|
| 3,420,609 | 1/1969 | Kozawa | 356/340 |
| 3,659,946 | 5/1972 | Kozawa et al. | 356/340 |
| 4,565,446 | 1/1986 | Chu | 356/343 |

Primary Examiner—Richard A. Rosenberger
Attorney, Agent, or Firm—Philip J. Wyatt

[57] ABSTRACT

A method is disclosed based on a single injection into a modified HPLC line by which means the light scattering data required to characterize the injected molecular suspension in terms of its weight-average molecular weight, z-average square radius, and second virial coefficient may be measured and collected. The method requires that a molecular suspension at a fixed concentration be prepared and injected into a flowing stream of pure solvent following standard liquid chromatographic procedures. The sample is then passed directly to a mixing chamber whose volume is preferably several times that of the injected volume. After this mixing, the sample enters a light scattering detector where its absolute scattering intensity as a function of angle is measured for each eluting fraction. From the data so-recorded, the concentration of each fraction may be calculated and a Zimm plot may be made to yield the required molecular parameters.

6 Claims, 7 Drawing Sheets

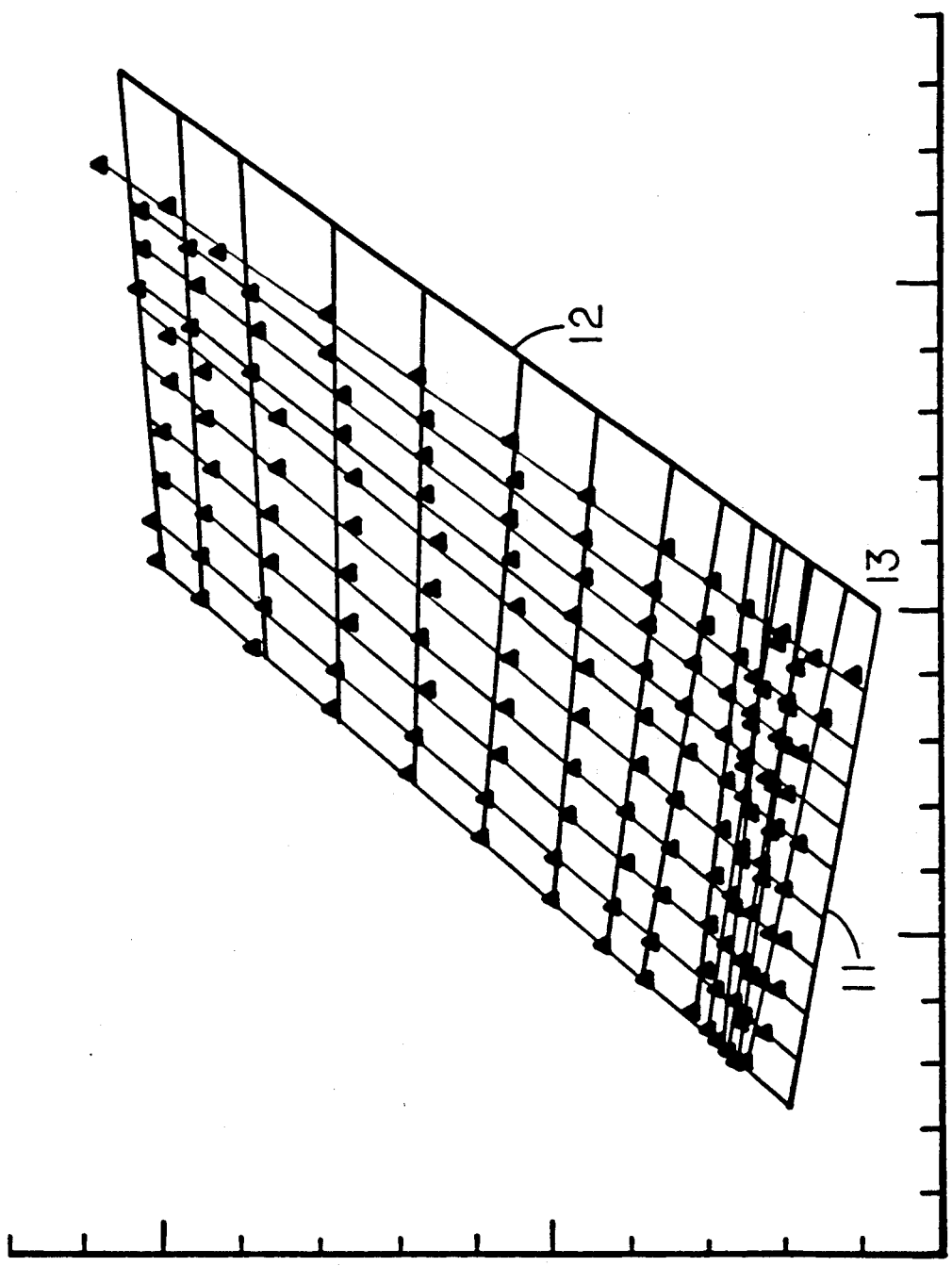

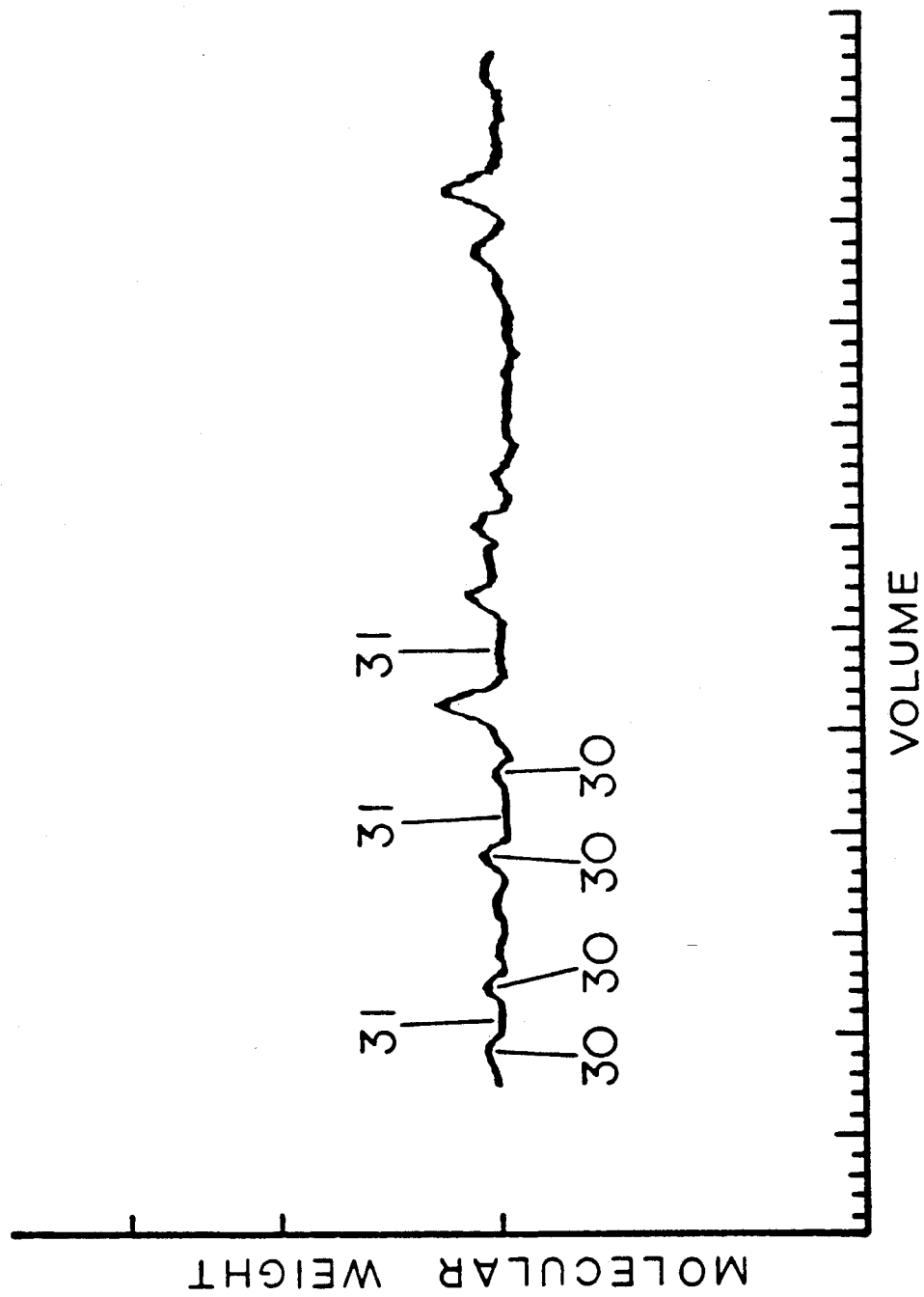

HIGH PERFORMANCE ZIMM CHROMATOGRAPHY—HPZC

RELATED PATENTS AND CO-PENDING APPLICATIONS

The present invention concerns a new method for the collection and processing of light scattering data needed to characterize molecules dissolved in a solvent. In order to apply this method, certain types of light scattering apparatus will be most useful to achieve the fullest implementation. The following applications and issued U.S. Patents describe apparatus of this type:

U.S. Pat No.: 4,541,719
Title: Method and Apparatus for Characterizing Microparticles and Measuring their Response to their Environment
Inventor: P. J. Wyatt
Date of Filing: July 20, 1982
Date of Issue: Sep. 17, 1985
Art Unit Number: 255

U.S. Pat. No.: 4,616,927
Title: Sample Cell for Light Scattering Measurements
Inventors: S. D. Phillips, J. M. Reece, and P. J. Wyatt
Date of Filing: Nov. 15, 1984
Date of Issue: Oct. 14, 1986
Art Unit Number: 255

U.S. patent application Ser. No.: 07/380551
Title: Light Scattering Cell With Manifolds
Inventors: P. J. Wyatt and R. F. Schuck
Date of Filing: Feb. 21, 1989
Preliminary Class: D10-103.000

U.S. Pat. No.: 4,907,884
Title: Sample Cell Monitoring System
Inventors: P. J. Wyatt and S. D. Phillips
Date of Filing: Jun. 5, 1987
Date of Issue: Mar. 13, 1990
Art Unit Number: 255

U.S. Pat. No.: 4,952,055
Title: Differential Refractometer
Inventor: P. J. Wyatt
Date of Filing: Oct. 3, 1988
Date of Issue: Aug. 28, 1990
Art Unit Number: 255

U.S. patent applicationm No.: 07/499479
Title: Differential Refractometer
Inventor: P. J. Wyatt
Date of Filing: May 25, 1989
Continuation-in-Part of U.S. Pat. No. 4,952,055.

BACKGROUND

The determination of molecular weights and sizes from light scattering measurements has been an important procedure since the mid-1940's. The general method for making these determinations was established by Zimm [J. Chem. Phys. 16, 1099 (1948)] and consists of preparing a series of molecular suspensions, each at a different concentration, and then measuring the excess scattering of each suspension as a function of scattering angle. From these measurements and numerical extrapolations of the data to zero scattering angle and zero concentration, the so-called weight-average molecular weight, $M_w$, z-average square radius, $<r_g^2>$, and second viral coefficient, $A_2$, are determined for the molecules in the suspension. The second quantity is often referred to as the mean square radius or by the misnomer square "radius of gyration."

At very low concentrations, c, the weight-average molecular weight $M_w$ of molecules in a suspension may be derived from measurements of the suspension's light scattering properties by $$\frac{R(\theta)}{K^* c} = M_w P(\theta)[1 - 2A_2 M_w c P(\theta)], \quad (1)$$

where the excess scattered intensity ratio at each scattering angle $\theta$ $$R(\theta) = f[I(\theta) - I_s(\theta)]/I_0. \quad (2)$$

Here $I(\theta)$ is the measured intensity of scattered light from the suspension at an angle $\theta$, $I_s(\theta)$ is the corresponding quantity for the pure solvent, $I_0$ is the incident light flux, and f is an absolute calibration constant. The second virial coefficient is $A_2$. For vertically polarized incident light of vacuum wavelength $\lambda_0$, the constant $$K^* = (2\pi n_0 dn/dc)^2/(N\lambda_0^4), \quad (3)$$

where N is Avogadro's number, $n_0$ is the refractive index of solvent and the refractive index increment is dn/dc. This latter quantity represents the change of solution refractive index, dn, for a change of molecular concentration dc.

Debye showed in general that the angular intensity variation, $P(\theta)$, is of the form $$P(\theta) = 1 - a_1 x + a_2 x^2 - a_3 x^3 + \ldots, \quad (4)$$

where $$x = (2k \sin \theta/2)^2, \quad (5)$$

and $k = 2\pi n_0/\lambda_0$. The leading coefficient, $a_1$, is easily shown to be $$a_1 = <r_g^2>/3, \quad (6)$$

where the square mean radius, or z-average square radius, is given by $$\frac{R(\theta)}{K^* c} = M_w P(\theta)[1 - 2A_2 M_w c P(\theta)], \quad (1)$$

the integration being taken over all mass elements dM of the molecule with respect to its center of gravity.

Zimm considered the reciprocal form of Eq. (1) at small values of u in the form $$K^* c/R(\theta) \approx \frac{(1 + u)}{M_w} + 2A_2 c \quad (8)$$

The parameter $u = <r_g^2> x/3$ is always small in the limit as $\sin^2\theta/2 \to 0$. Note that in the limit as c goes to 0 and $u \to 0$, setting $y = K^* c/R_\theta$ $$y_0 = K^* c/R(0) = 1/M_w, \quad (9)$$

i.e. the intercept yields the reciprocal weight average molecular weight. Setting $y = K^* c/R(\theta)$, we note further that in the limit as $c \to 0$, $$dy/d(\sin^2\theta/2) = (2k)^2 <r_g^2>/(3M_w). \quad (10)$$

i.e. the initial slope of the extrapolated $c=0$ data will yield the z-average square radius directly when Eq. (10) is combined with Eq. (9). In addition, in the limit as $\sin^2\theta/2 \to 0$, $$dy/dc = 2A_2, \quad (11)$$

i.e. the initial slope of the extrapolated $\sin^2\theta/2=0$ data will yield the second viraial coefficient. Zimm implemented these results graphically by means of the so-called Zimm plot technique. The process consists of plotting the experimentally measured values of $K^*c/R(\theta)$ against $\sin^2\theta/2 + Sc$, where S is an arbitrary "stretch" constant selected for convenience in making the plots so that the Sc values are comparable in magnitude to the $\sin^2\theta/2$ values.

Historically, these measurements have been difficult to perform because of the requirement that the prepared solutions be essentially free of dust. The presence of even minute amounts of dust often can result in spurious scattering that may overwhelm the scattering signals of the molecules themselves, especially in the forward scattering directions. The most time consuming elements of the light scattering measurement process is preparing the series of molecular dilutions, each free of dust. While the light scattering measurements themselves may only require a few minutes using modern multiangle light scattering photometers, the sample preparation may require manny hours or even days.

With the introduction of size exclusion and other types of chromatography which are combined with an in-line multiangle light scattering detector, it has become possible to measure the weight-average molecular weight and z-average square radius for each eluting fraction as long as the corresponding concentration of each fraction is known. This is usually achieved by an in-line concentration detector. The chromatographic separation is achieved by means of a packed column, for the ease of size exclusion chromatography, or a channel with an externally applied transverse field, for the case of field flow fractionation chromatography, etc. Only a single concentration is required to be injected in the chromatographic procedure, with the column or channel separating the sample, for example, by the hydrodynamic size of its molecular constituents. These techniques are quite useful in removing the effects of dust since dust, generally being of a greater size than the molecules, is separated and isolated from the molecules by the column. Most importantly, however, preparation of only a single concentration is required which is much easier to preparae than an entire series. Although such chromatographic separation can provide further information about the molecules, such as mass and size distributions, this detail may not be required for many applications. In addition, the chromatographic separation per se requires an injector, column, light scattering detector, and concentration detector, together with several chromatographic system elements such as pumps, filters, dampers, etc.

A simple method for determining weight average molecular weights, z-average square radii, and second virial coefficients has been developed that combines some elements of on-line chromatographic separation with the standard batch sample procedures described by Zimm. Although the concept of injection of a sample without a column seems to be an attractive means to produce a concentration gradient by dilution, with an in-line light scattering detector and an in-line concentration detector being used to provide the light scattering data at the several concentrations required for application of the Zimm technique, the concept has two basic shortcomings. First is the problem that during flow through a capillary or channel, a molecular sample may separate somewhat on the basis of the hydrodynamic radii of its constituents and the laminar flow of the stream. The molecular weight distribution must be identical in each eluting fraction (at each concentration) for application of the method. The second major obstacle to implementing this injection method is the so-called band broadening effect. Because of continuous dilution effects during the sample flow from the injector through the light scattering detector and through the concentration detector, the concentration profile will not match the light scattering profile. Because of these so-called band broadening effects, the derived concentration profile of the diluted eluting sample would not be accurate.

Many others have used light scattering measurements for the on-line characterization of particulates. These include Takeda, et al. in U.S. Pat. No. 4,957,363 who describe the use of multiwavelength measurements on flowing samples; Webb, et al. in U.S. Pat. No. 4,664,513 who describe seeding a flowing stream with reflective spherical particles to monitor local vorticities via the light scattering of the particles; Hattori in U.S. Pat. No. 4,264,206 who describes a dust counter based on measuring scattered light from particles in an air stream; Wertheimer in U.S. Pat. No. 4,265,538 who describes a special flow cell for making light scattering measurements at three mutually orthogonal directions from a flowing stream; and, Steen, in U.S. Pat. No. 4,915,501 who describes a flow cytomer strucutre permitting measurement of light scattered into two different angular ranges from microscopic particles and biological cells.

In his U.S. Pat. No. 3,850,525, Kaye describes means to measure the scattering of light into two directions from a small sample that may be measured in a static or flowing mode. He also discusses how these measurements combined with Zimm's implementation may be used to determine molecular parameters. Chu, in his U.S. Pat. No. 4,565,446, describes a cell configuration whereby scattered light may be measured from a fluid passing therethrough at two scattering angles. He also discusses requirements for making Zimm plots from samples at different angles. Neither of the two aforementioned patents discloses means for making on-line Zimm plots, but only the need to make measurements in the absence of background and efforts to reduce said background interferences.

The basic U.S. Pat. No. 3,522,725 of Waters describes common operating principles of liquid chromatographs. He does not discuss Zimm plots nor their posssible implementation in his chromatrographic instrument since it does not contain light scattering and detection means. The inclusion of a refractive index detector, a standard element often used to monitor molecular concentrations, is disclosed together with the special environmental contraints required to ensure that its output remains stable.

SUMMARY OF THE INVENTION

The method for deriving molecular characterization parameters from a single molecular suspension consists of injecting the suspension into a standard high performance liquid chromatography (HPLC) line through which a solvent is being pumped. In the preferred embodiment of this invention, the injected solution is pumped through standard chromatographic tubing to an in-line mixer placed in series with and immediately following the injector and a short distance from the light scattering detector. The latter measures the absolute scattered light intensity at one or more angles for each elution fraction or "slice" of the remixed sample. At least two light scattering detectors at different scattering angles are required if any size information is to be derived. From the light scattering signals, both the concentration profile of the eluting sample and its molecular parameters may be derived therefrom following the procedure of Zimm. If a standard concentration detector be connected serially following the light scattering detector, then a value proportional to the molecular weight of the sample may be calculated as a function of elution volume. From these values the eluting slices containing large contributions of dust or molecular aggregates may be identified explicityly for later removal during data processing. The three key inventive elements of this process are: 1) the sample remixing immediately before measurement to counteract any separations that may have occurred due to flow conditions: 2) the use of one of the light scattering detectors to monitor concentration in the absence of a concentration detector; and, if the sample contains sources of noise such as dust, 3) the ability to minimize the effects of dust or aggregates by incorporating a concentration sensitive detector and reprocessing the data after selecting concentrations from regions of the elution that have small or negligible fluctuations in the earlier calculated values proportional to the weight-average molecular weight of each eluting fraction.

BRIEF DESCRIPTION OF THE DRAWINGS

FIG. 6 is a Zimm plot derived from the measurement at several scattering angles of a remixed sample of polystyrene.

FIG. 7 shows the variationof molecular weight of a remixed sample as a function of retention volume using an on-line concentration detector.

DETAILED DESCRIPTION OF THE INVENTION

Figure 1:
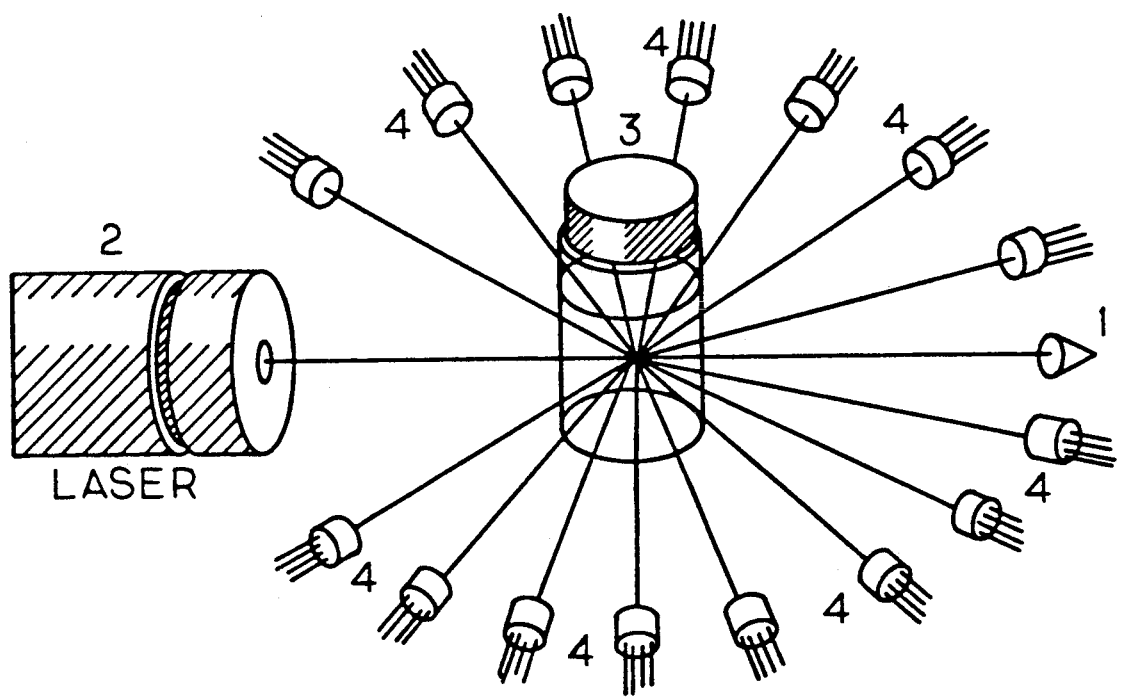
FIG. 1 is a schematic representation of a traditional batch light scattering measurement.

FIG. 1 presents a schematic representation of a traditional, batch mode light scattering measurement. A molecular suspension is illuminated by a fine monochromatic light beam 1. Typically, the light source is a laser 2 producing vertically polarized light. The molecular suspension is contained in a transparent cuvette 3 surrounded by an arrayy of collimated detectors 4 each at a different angle with respect to the incident beam. Alternatively, a single collimated detector may rotate in a plane about the sample. If the deduction of molecular size is not required, then measurement at a single, low angle will be sufficient. At each angle and for each concentration of the suspension, a value of $K^*c/R(\theta)$ may be determined. From these data one would make a Zimm plot such as shown for four concentrations 5, 6, 7, 8 in FIG. 2. Note the extrapolations to zero angle 9 of each different concentration series and the extrapolation to zero concentration 10 of each of the 15 angles. The two corresponding limiting lines 11 and 12 drawn through these limiting sets of points are then extrapolated to their common intercept 13.

Figure 2:
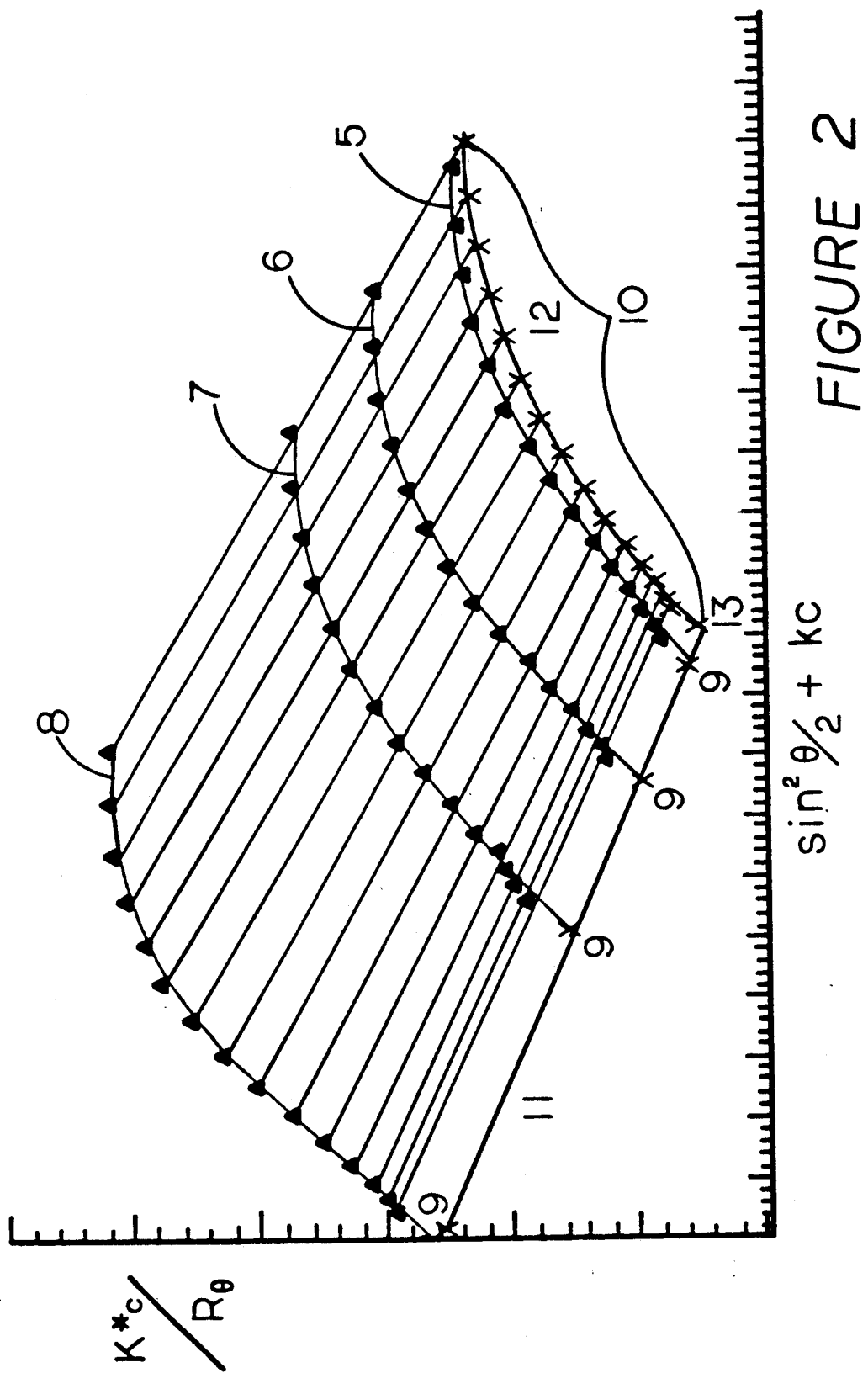
FIG. 2 is a typical Zimm plot using a negative stretch factor.

For the Zimm plot of FIG. 2, the intercept 13 corresponds to a molecular weight of 211,000. The four concentrations used were $3.625 \times 10^{-5}$, $1.865 \times 10^{-4}$, $3.626 \times 10^{-4}$, and $7.6 \times 10^{-4} = g/ml$. The solvent used tetrahydrofuran whose refractive index is 1.404 at the incident laser wavelength of 632.8 nm. The refractive index increment, dn/dc, for the dissolved polymer was 0.35. Measurement of the slopes of the extrapolated curves near the origin 13 yielded $$<r_g^2>^{\frac{1}{2}} = 43 \text{ nm and } A_2 = 6.9 \times 10^{-4} \text{ ml mol/g}^{21}. \quad (12)$$

The same results may be calculated directly by various analytical means using these same data. For example, the extrapolated plots may use Eq. (1) directly rather than its reciprocal, Eq. (8). In some formulations, the suitably expanded square root of both sides of Eq. (8) is plotted. The so-called Simplex and related methods may be employed whereby the parameters of Eqs. (1) or (8) are fitted in at least squares sense.

Figure 3:
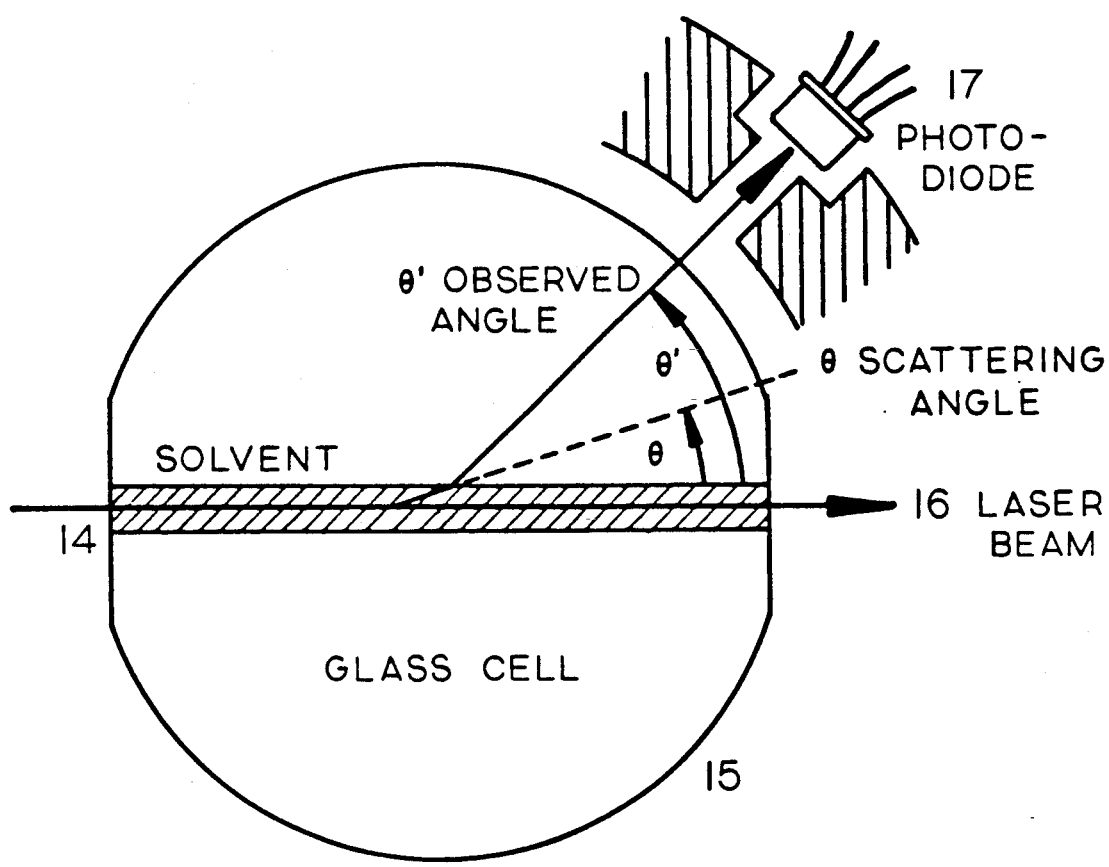
FIG. 3 shows the light scattering measurement of a preferred embodiment of the invention.

It is the object of our invention to be able to derive similar molecular parameters on the basis of a single concentration injected into a chromatographic line. The measurements of scattered light intensities are therefore made as the sample flows through a region circumscribed by an array of detectors. FIG. 3 shows a flow cell of a preferred embodiment disclosed in U.S. Pat. No. 4,616,927 wherein the solution flows through a small capillary 4 bored through a diameter of a cylindrical glass cell 15. Parallel to and passing through the center of this bore is a fine light beam 16. Further details of this structure are discussed in U.S. Pat. No. 4,616,927. Collimated photodetectors 17, one of which is shown in FIG. 3, surround the cell. The detectors may be photodiodes, photomultipliers, or other photosensitive devices able to measure the relative intensity of light scattered into the fixed directions centered on the scattering angles $\theta$ with respect to the forward detection. Because of refraction, the collimated detectors fixed at angles $\theta'_i$ ($i = 1, \ldots, m$, the number of detectors employed) define the scattering angles actually measured, $\theta_i$, through application of Snell's Law $$n_g \sin(\pi/2 - \theta'_i) = n_s \sin(\pi/2 - \theta_i) \quad (13)$$

or $$n_g \cos \theta'_i = n_s \cos \theta_i, \quad (14)$$

where $n_g$ and $n_s$ are the refractive indices of the glass and solvent, respectively. Many other flow cell configurations are possible as would be familiar to those skilled in the art of light scattering measurements. Among them are cylindrical capillary flow tubes whereby the incident light beam would strike the inner capillary along a diameter and perpendicular to the direction of flow and those of Chu Kaye referenced earlier.

Figure 4:
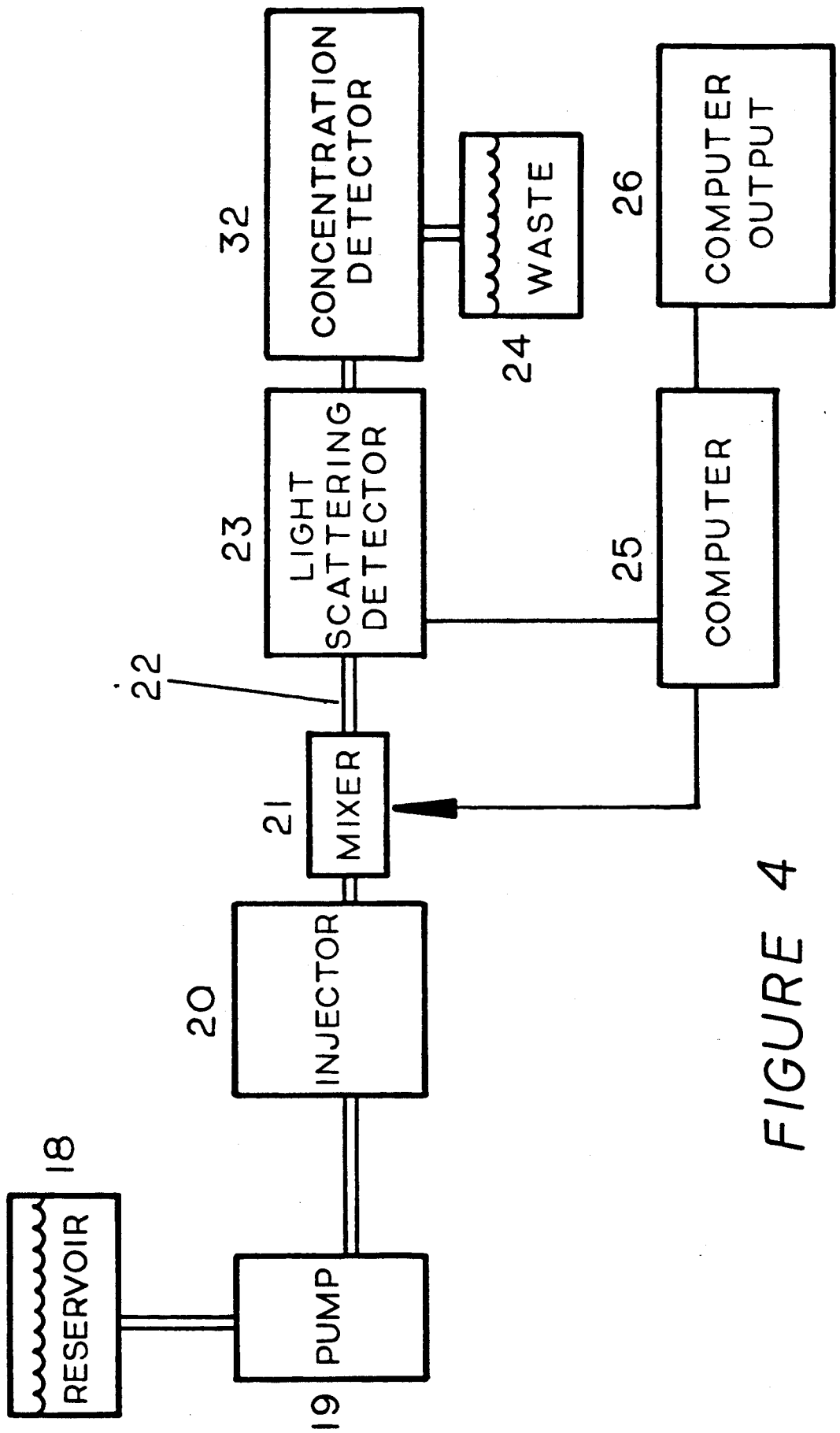
FIG. 4 shows the chromatographic connections and elements required for application of the method.

FIG. 4 shows the preferred configuration to employ the method of this invention. A reservoir 18 provides solvent for the in-line pump 19 which continually or intermittently pumps the solvent through an injector 20 from where it passes into an in-line mixer 21 of the type manufactured by The Lee Company. The mixer is necessary to recombine any injected sample that may have separated because of its passage through the capillary tubing 22. In its preferred embodiment, the mixer volume should be several times the volume of the injected sample and connecting capillary 22 combined. This insures that all or most of any molecular fractions lagging the main sample are remixed before passing into the light scattering detector 23. An in-line filter of small aperture is generally placed before the injector to remove dust, if any, from the solvent. In addition, a second filter may be placed after the injector as long as such filter does not remove or otherwise affect any of the solute molecules.

The excess scattered intensity of Eq. (2) is preferably measured many times at each detector and all such values are converted into numerical representations by means of a multichannel analog-to-digital converter of the types manufactured by Data Translation Corporation. The analog-to-digital converter may reside in a personal computer 25 or be included as part of the light scattering detector system. The number of times the measurements are made and the frequency of measurement are generally selected by the user program and controlled by the computer. A particular set of measurements, performed during a short period of time during which a small volume $v$ of the sample has passed through the scattering region, may be processed to minimize noise and/or averaged. The volume $v$ is called a chromatographic slice or simply a slice. At each slice i, a corresponding processed excess scattered intensity ratio $R(\theta_j)$ at each detector angle $\theta_j$ is calculated and saved for latter analysis and display on a computer output device 26 such as a video display screen, a printer, or rotary recording means such as a floppy, hard, or optical disk.

From an off-line batch measurement of dn/dc, the left hand side of Eqs. (1) or (8) may be calculated for each slice i provided the concentration $c_i$ be known at that slice also. The inventive method herein described provides an immediate means by which such concentratoon may be derived at each slice i by recording the excess scattered intensity ratio $R(\theta_k)$ at a single detector k. For an unseparated sample at very low concentration, $R(\theta_k)$ is directly proportional to $N_i M_w^2$, where $N_i$ is the number of molecules per ml in that slice per ml and $M_w$ is the weight average molecular weight of the sample. Thus $$R(\theta_k) = \beta N_i M_w^2, \qquad (15)$$

where $\beta$ is a constant. Noting that $$N_i M_w = c_i \, gms/mL \qquad (16)$$

Eq. (15) may be rewritten $$R(\theta_k) = \beta c_i M_w \qquad (17)$$

It is important to the success of this proposed method that the interaction between molecules in the suspension be very small so that the second term on the right-hand side of Eq. (8) may be dropped. Only in this event will Eq. (15) be valid.

The concentration of each slice is therefore $$c_i = R(\theta_k)/(\beta M_w). \qquad (18)$$

However, $$\sum_i c_i = \frac{1}{\beta} \sum_i R(\theta_k)/M_w = \frac{1}{(\beta M_w)} \sum_i R(\theta_k) = W_I/v, \qquad (19)$$

where $W_I$ is the total mass injected and $v$ is the volume of each slice. Thus $$\beta M_w = (v/W_I) \sum_i R(\theta_k), \qquad (20)$$

and therefore $$\begin{aligned} c_i &= R(\theta_k)/(\beta M_w) \\ &= \frac{R(\theta_k) W_I/v}{\sum_j R(\theta_k)}, \end{aligned} \qquad (21)$$

from Eq. (18). Thus the concentration at any slice $v$ may be determined from measurements taken at one angle only, $\theta_k$.

Once the $c_i$ are calculated from Eq. (21), all elements are available to derive a Zimm plot or other means by which the molecular parameters may be derived. Again, the success of this method will depend critically on the validity of Eq. (8), and, additionally, that the angle $\theta_k$ at which the $R(\theta_k)$ are measured to determine the concentration is such that $$2A_2 c_i << \frac{1 + u(\theta_k)}{R(\theta_k)}, \qquad (22)$$

i.e. that the second term of Eq. (8) may be dropped at all slices i. At the very low concentrations common in most chromatographic injections, and subsequent dilutions, this approximation will be generally true. In the preferred embodiment of this invention, $\theta_k$ is selected at 90°.

If we compare Eqs. (17) and (8), taking into account Eq. (22), we find $$\beta = K^*/[1 + u(\theta_k)] \qquad (23)$$

Figure 5:
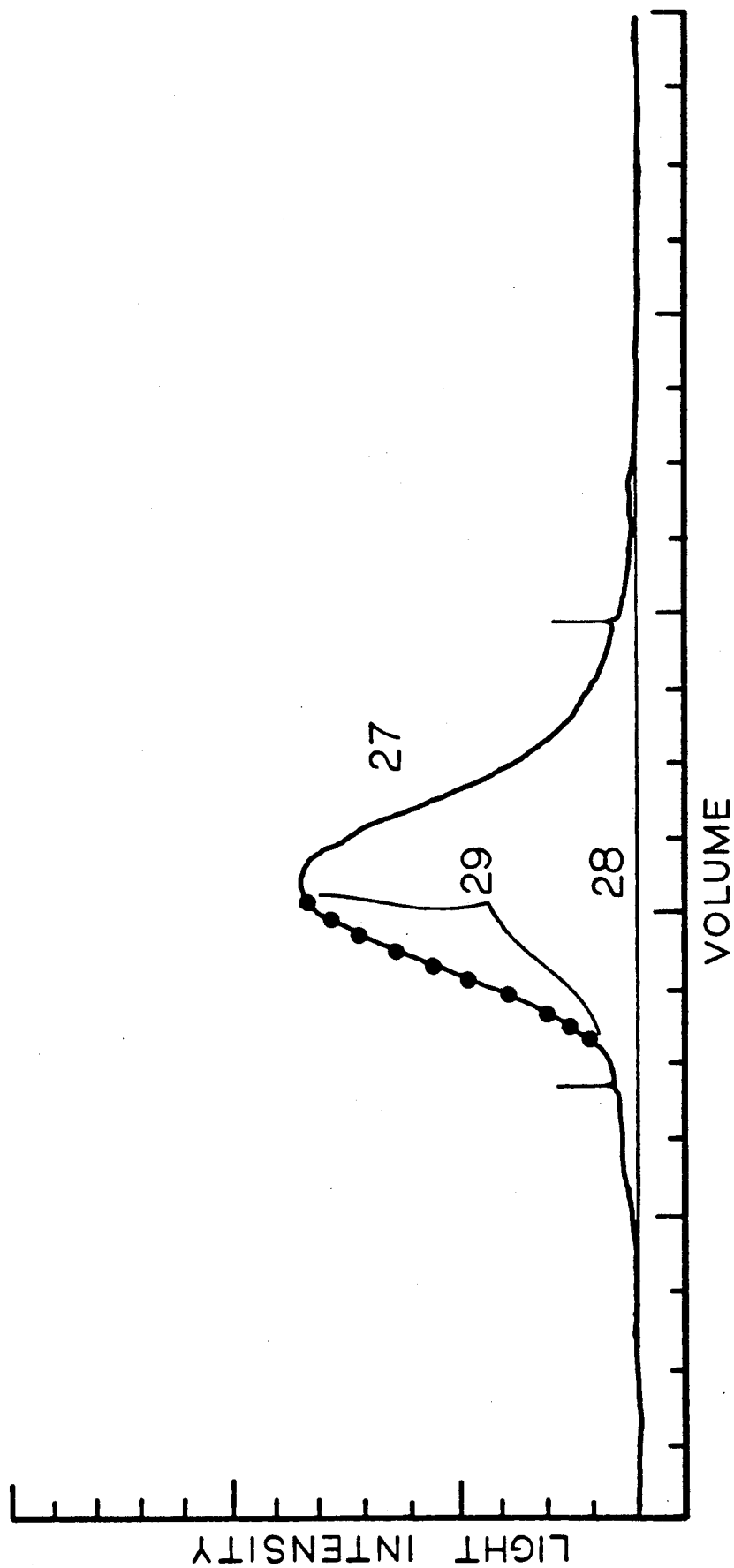
FIG. 5 is the chromatographic light scattering signal profile at 90° from a remixed injected sample.

FIG. 5 presents a chromatogram 27 measured at 90° by a multiangle light scattering photometer. The 20 $\mu$l injected sample was prepared at a polystyrene concentration of 0.003 gms/ml. The tetrahydrofuran solvent was pumped at a rate of 1.0 ml/minute into a 250 $\mu$l mixer. Slices were collected at one-second intervals with 50 measurements at each of 15 angles being made during that interval. The abscissa corresponds to the retention volume, i.e. the volume that has passed through the light scattering detector since to the initial injection. The baseline 28 had been drawn in this figure, as it would be for all other angles, by which means the computer calculates the average excess scattering $R(\theta_j)$ at each slice i and angle j per Eq. (2). The marked indicia 29 in the figure correspond to the concentrations selected to generate the Zimm plot shown in FIG. 6. Generally, data are averaged over several slices about the selected points. For the data of FIG. 5, this value was five. This averaging process reduces the fluctuations of the collected data.

FIG. 6 shows a Zimm plot based on the data collected at each angle $\theta_j$ for the concentrations indicated in FIG. 5. Note the $c=0$ extrapolated curve 12 and $\sin^2\theta/2=0$ extrapolated curve 11, respectively, and note the similarities with FIG. 2. The intercept 13 with the ordinate yields the reciprocal molecular weight, while the slopes of curves 11 and 12 near the intercept yield the second virial coefficient and z-average square radius, respectively, per the corresponding Eqs. (11) and (10).

FIG. 7 shows the calculated values proportional to weight-average molecular weights at each slice calculated from Eqs. (8) and (9) with terms of order $c A_2$ dropped. Note that an additional in-line concentration sensitive detector was required to derive this plot. Alternatively, data from the individual slices may be examined and those exhibiting noise eliminated from the calculations. Although said additional detector is not required for our invention, it does permit the identification of slices containing spurious noise such as would arise from dust or aggregates. Note the small fluctuations 30 in the data arising from dust or small molecular aggregates. If the sampels contain such aggregates or dust, their scattering effects may be minimized by adding a guard column or filter immediately before the remixer. Such devices may affect the molecules by shearing or removing part of the sample itself. The former situation will cause degradation of the derived molecular weights, while the latter circumstance can affect the accuracy of the derived molecular concentrations $c_i$. Equation (20) requires that the entire injected mass $W_I$ be recovered and accounted for in the collected data. If part of the injected mass does not reach the light scattering detector, the derived concentrations would be too small and the associated weight average molecular weight $M_w$ too large. The most direct way to reduce molecular weight fluctuations is to process the data a second time selecting concentrations from those regions of the derived data of FIG. 7 that lie on or near the baseline envelope 31 of the data. Restricting the selection of slices to these regions or regions of relatively small fluctuations will insure improved precision of the derived results without the need to filter. Even without the in-line concentration detector, the examination of the $R_{\theta i}$ vaues versus $\theta_i$ for each slice will permit the detection of anomalous regions wherein the $R_{\theta i}$ include spurious points arising from dust or aggregates. After such a preview, slices containing aggregate or dust abberations may be eliminated.

Now whereas hereinbefore we have described a preferred method for the derivation of molecular characteristics, there will be evident to those skilled in the art of light scattering measurement many variations of our method clearly anticipated in our descriptions. Certainly among these is the measurement at only a single low scattering angle such as described by Kaye. Since no angular variation of scattered intensities are measured by such instruments, no molecular size information may be derived. However, for many practical applications, the determination of the weight average molecular weight and second virial coefficient will be sufficient.

We claim:

1. A method for deriving the weight-average molecular weight, z-average square radius, and second virial coefficient of a molecular suspension comprising the steps of:
   a. Preparing a single concentration of said molecular suspension;
   b. Injecting a small aliquot of said suspension into a chromatographic tubing through which flows a solvent, said solvent diluting said aliquot at its leading and trailing edges as it is pumped through said tubing;
   c. Remixing said injected aliquot by means of an in-line mixer of volume larger than the injected aliquot;
   d. Illuninating said remixed aliquot with a fine beam of light as the injected aliquot flows through the scattering volume of a sequentially connected in-line light scattering photometer;
   e. Measuring the excess scatttered intensity ratio $R_i(\theta_j)$ at each scattering angle j of said photometer and each slice i;
   f. Selecting the excess scattered intensity ratio for each slice i at a single detector scattering angle $\theta_j$ of the illuminated remixed aliquot;
   g. Deriving the concentration $c_i$ for the sample at each slice i from the relation $$c_i = \frac{W_I R_i(\theta_k)}{nu \sum_j R_j(\theta_k)}$$

where $W_I$ is the total injected mass and $R_i(\theta_k)$ is the excess scattered intensity at said selected detector scattering angle $\theta_k$ and $v$ is the volume of each slice;
   h. Selecting, from a set of different slices i spanning a range of derived concentration values $c_i$, the excess scattered intensity ratios $R_i(\theta_j)$ at each of the measured i slices and each scattering angle $\theta_j$;
   i. Deriving the weight-average molecular weight, z-average square radius, and second virial coefficient from said selected measurements and associated derived concentrations following the procedure of Zimm.

2. The method of claim 1 where each of said excess scattered intensity ratios $R_i(\theta_i)$ selected for application of said procedure of Zimm is an average of $R_i(\theta_i)$ values over a number n of slices adjacent to each j value selected.

3. The method of claim 1 where said fine beam of light is from a laser.

4. The method of claim 3 wherein said fine beam of light is vertically polarized.

5. The method of claim 1 where said fine beam of light is monochromatic.

6. The method of claim 1 where a concentration detector is sequentially connected in-line following said light scattering photometer and the concentration value measured by said in-line concentration detector is used to calculate the weight averaged molecular weight, $M_w$, of each eluting slice from the relation $$K^*c/R(0)=1/M_w$$

where $R(0)$ is the excess Rayleight ratio of the light scattering measurement extrapolated to zero scattering angle, and $$K^*=(2\pi n_0 dn/dc)^2/(N\lambda_0^4),$$

N is Avogadro's number, $n_0$ is the index of refraction of the solvent, and $dn/dc$ is the refractive index increment; and said calculated variation of molecular weight with elution volume is used to identify those slices containing spurious noise such as would arise from dust or aggregates, permitting thereby the selection of said set of different slices spanning said range of derived concentration values sufficient to derive said weight averaged molecular weight, z-averaged square radius and second virial coefficient from said selected measurements following the procedure of Zimm.

* * * * *